United States Patent
Nies et al.

(10) Patent No.: US 9,572,668 B2
(45) Date of Patent: Feb. 21, 2017

(54) IMPLANT MADE OF A FIBER COMPOSITE MATERIAL

(71) Applicant: Innotere GmbH, Radebeul (DE)

(72) Inventors: Berthold Nies, Fränkisch-Crumbach (DE); Sophie Rössler, Dresden (DE); Sandra Storch, Moritzburg (DE); Chokri Cherif, Dresden (DE); Ezzeddine Laourine, Albstadt (DE)

(73) Assignee: Innotere GmbH, Radebeul (DE)

( * ) Notice: Subject to any disclaimer, the term of this patent is extended or adjusted under 35 U.S.C. 154(b) by 72 days.

(21) Appl. No.: 14/391,711

(22) PCT Filed: Apr. 11, 2013

(86) PCT No.: PCT/EP2013/057637
§ 371 (c)(1),
(2) Date: Oct. 10, 2014

(87) PCT Pub. No.: WO2013/153185
PCT Pub. Date: Oct. 17, 2013

(65) Prior Publication Data
US 2015/0066144 A1 Mar. 5, 2015

(30) Foreign Application Priority Data
Apr. 11, 2012 (DE) .................. 10 2012 205 888

(51) Int. Cl.
*A61F 2/28* (2006.01)
*A61L 27/42* (2006.01)
*A61L 31/12* (2006.01)

(52) U.S. Cl.
CPC ............ *A61F 2/28* (2013.01); *A61L 27/427* (2013.01); *A61L 31/124* (2013.01); *A61L 2430/02* (2013.01)

(58) Field of Classification Search
CPC A61F 2/28; A61F 2002/2835; A61F 2/30965; A61F 2002/30963
See application file for complete search history.

(56) References Cited

U.S. PATENT DOCUMENTS 4,230,455 A 10/1980 Hidaka et al.
4,693,721 A * 9/1987 Ducheyne ........... A61F 2/30907
419/24

(Continued)

FOREIGN PATENT DOCUMENTS

CN 102085123 6/2011
WO 2006/039733 A2 4/2006

(Continued)

*Primary Examiner* — Brian Dukert
(74) *Attorney, Agent, or Firm* — Michael Soderman

(57) ABSTRACT

The invention relates to an implant and a set for producing an implant and their uses. Furthermore, the invention describes a method of making an implant as per the invention. An implant for producing bone implants with improved mechanical characteristics, especially with adjustable mechanical characteristics, is provided via the invention. The implant as per the invention made up of a fiber composite material contains resorbable mineral bone cement as the matrix material, to which reinforcing, long metal fibers and/or endless metallic fibers with an aspect ratio of at least 100:1 are added in the form of at least one fiber structure that provides a framework and that preforms the contour of the implant.

18 Claims, 3 Drawing Sheets

(56) References Cited

U.S. PATENT DOCUMENTS

| | | | |
|---|---|---|---|
| 6,955,716 B2 | 10/2005 | Xu | |
| 2005/0208094 A1* | 9/2005 | Armitage | A61K 31/74 424/423 |
| 2011/0144764 A1* | 6/2011 | Bagga | A61F 2/28 623/23.61 |

FOREIGN PATENT DOCUMENTS

| | | | |
|---|---|---|---|
| WO | 2011137292 A2 | 11/2011 | |
| WO | 2011157758 A1 | 12/2011 | |

* cited by examiner

IMPLANT MADE OF A FIBER COMPOSITE MATERIAL

CROSS-REFERENCE TO RELATED APPLICATIONS

This application is the U.S. national stage of International Application No. PCT/EP2013/057637 filed on Apr. 11, 2013, and claims the benefit thereof. The international application claims the benefit under 35 USC 119 of German Application No. DE 10 2012 205 888.5 filed on Apr. 11, 2012; all applications are incorporated by reference herein in their entirety.

BACKGROUND OF THE INVENTION

The invention relates to an implant, a bone implant, which contains an implant as per the invention and a set for production of an implant and their uses. Furthermore, the invention describes a method of making an implant as per the invention.

There has long since been a need in orthopedics and surgery to fill in bone defects again after fractures, or an amputation as a result of tumor diseases or inflammation, with bone material or a replacement that is similar to bone. CN 102085123 A discloses a dual-component implant in connection with this that consists of a non-woven titanium wedge-wire cylinder that is filled in with a bone replacement material in an interlocking way. The bone replacement material consists of a course-grained calcium phosphate cement constituting 40 to 94% of the mass by weight and a binding material constituting 5 to 29% of the mass by weight. The two cylinder heads of the non-woven titanium wire cylinder are closed up with biodegradable casing caps; the natural bone tissue can grow from the cylinder ends into the implant because of that. The non-woven titanium wedge-wire cylinder is consequently not included in the bone replacement material, but instead only serves as a filling container.

Materials with high mechanical stress-bearing capacities are required for the implantation, especially implantation in bone. The addition of a mesh structure to polymethyl methacrylate cements to improve their mechanical characteristics is a known procedure. U.S. Pat. No. 4,064,567 discloses a joining system between bone and an implant for this that includes a mesh structure made, for instance, of non-resorbing metals, plastic or carbon or resorbable fibers such as Dacron. The mesh structure is filled with a polymethyl methacrylate cement and is intended to serve in improving the fixation of prostheses and, among other things, avoiding fracture points.

Moreover, the aim is to use materials in implants that promote the ingrowth of the natural bone tissue (that are therefore bioactive) and that are successively eliminated in the body (that are therefore resorbable), in order to avoid a later removal of an implant. Mineral bone cements, for instance based on calcium phosphates, are commonly used as bioactive and resorbable materials. It is possible to create mineral bone cements with high compressive strength, but implants made of a pure mineral bone cement can only be subjected to a very low level of bending stress.

The reinforcement of mineral bone cements with resorbable polymer fibers to improve the mechanical characteristics of implants based on mineral bone cements is a known procedure. The mechanical characteristics of the implants based on mineral bone elements can be improved because of that, but the compressive strengths and bending strengths are still inadequate.

U.S. Pat. No. 6,955,716 B2 discloses a calcium phosphate bone replacement material here that constitutes more than 20% of the mass by weight of non-metallic, resorbable fibers. The non-metallic, resorbable fibers are mainly selected from polymer fibers, for instance Vicryl threads, polyglactin 910, Ethicon, Somerville, N.J.; Panacryl™ threads, Ethicon, N.J.; or ceramic silicon carbide fibers.

Filling resorbable, mineral bone cement into open-cell metal structures such as foams or hollow-sphere structure made of metal to improve the mechanical characteristics of implants based on mineral bone cements is a known procedure. A bone implant of that type is disclosed in WO 2008/064672; a resorbable mineral bone cement based on calcium phosphates and/or magnesium phosphates is filled into a metallic foam or a metallic hollow-sphere structure in an at least a partially interlocking way. Metallic structures are chosen for this whose rigidity is in the range of healthy, cortical human bone. High compressive strength of the implant is already made possible at the point in time of the implantation because of the metallic structure. Bone tissue successively grows into the implant because of the resorbability of the mineral bone cementer; the remaining metal with rigidity comparable to that of healthy bone remains. A drawback of the metal foams or metal hollow-sphere structures that are used is that the mechanical characteristics can only be adjusted in a limited way. A targeted adjustment of mechanical characteristics is not possible; rather, these metal structures have the same stress characteristics when there is stress from any arbitrary direction.

WO 2011/157758 A2 discloses a bone implant that consists of a resorbable material containing magnesium with a corrosion-resistant coating made of magnesium ammonium phosphate and a mineral bone cement. The material containing magnesium can be in the form of a centrally placed wire and/or diffusely distributed chips.

There is therefore a need to provide implants with adjustable stress characteristics that have, in particular, high bending strength and high compressive strength.

SUMMARY OF THE INVENTION

The invention relates to an implant and a set for producing an implant and their uses. Furthermore, the invention describes a method of making an implant as per the invention. An implant for producing bone implants with improved mechanical characteristics, especially with adjustable mechanical characteristics, is provided via the invention. The implant as per the invention made up of a fiber composite material contains
resorbable mineral bone cement as the matrix material, to which
reinforcing, long metal fibers and/or endless metallic fibers with an aspect ratio of at least 100:1 are added in the form of at least one fiber structure that provides a framework and that preforms the contour of the implant.

DETAILED DESCRIPTION

The object of the invention is to provide materials for the production of bone implants with improved mechanical characteristics, in particular with adjustable mechanical characteristics. A further object of the invention is to provide materials for use in bone implants that are easy to process and to flexibly use and that are suitable for achieving improved mechanical characteristics of the bone implants.

The problem is solved in accordance with the invention by an implant made of a fiber composite material that contains long metallic fibers and/or endless metallic fibers and resorbable mineral bone cement.

On top of that, the implant made of a fiber composite material includes:
 a) resorbable mineral bone cement as the matrix material in which
 b) reinforcing, long metallic fibers and/or endless metallic fibers with an aspect ratio of at least 100:1, in the form of at least one fiber structure providing a framework, are added to the fiber structure preforming the contour of the implant.

In so doing, the fiber structure providing a framework is adapted to take on directional stress on the implant for the defective area of the bone or joint that is to be repaired.

An implant in the sense of the invention is understood to mean a material that is suitable for implantation. The implant as per the invention is comprised of a fiber composite material that contains long metallic fibers and/or endless metallic fibers and resorbable mineral bone cement. Further components that are defined in more detail below can also be contained in the fiber composite material in addition to the metallic fibers and the resorbable mineral bone cement. In accordance with the invention, the long metallic fibers and/or endless metallic fibers are included in the mineral bone cement in the form of at least one fiber structure providing a framework; the metallic fibers are completely surrounded by the bone cement. The three-dimensional shape of a fiber structure providing a framework is preferably adapted to the defective area of the bone that is to be repaired.

Because of the use of resorbable mineral bone cements, they will be successively eliminated in the body after the implantation and the natural bone tissue can close the defective bone area that was treated.

Mineral bone cements in the form of a solid that does not easily dissolve in water are formed via the reaction of mineral bone cement powder and water. After the mixture of the mineral bone cement powder with water, a pasty mass is formed at first that successively hardens into a solid. To make the mixing easier, the mineral bone cement powder can also exist in a dispersed form in a water-free carrier fluid, therefore taking on the form of a water-free, pasty preparation, which will harden into a solid that does not easily dissolve after contact or mixture with water. All of the previously mentioned variants are included in the phrase "mineral bone cements" as defined by the invention, and thus the mineral bone cement powder (that has not yet reacted with water), a dispersion of the mineral bone cement powder in water, in an aqueous solution or in a water-free, non-aqueous carrier fluid, as well as the hardened solid. In an implant as per the invention, the resorbable mineral bone cement in the fiber composite material is therefore in the form of a solid (which was formed via the setting reaction of a mineral bone cement powder with water) or in the form of a paste (as a dispersion of the mineral bone cement power in water or an aqueous solution that successively hardens, or as a dispersion of mineral bone cement powder in a water-free and non-aqueous carrier fluid).

The term "mineral bone cement powder", in contrast, exclusively designates a powder that does not yet react with water here, which is suitable for forming a solid that does not easily dissolve after reaction with water.

Because of the reinforcing metallic fibers in the mineral bone cement as a matrix material, especially advantageous mechanical characteristics are achieved in the composite material product that are of higher quality in comparison with the mechanical characteristics of the individual materials. Since metallic fibers in the direction of the fibers can have strength that is many times higher than the same metal in a different form, it is possible to create materials with a high level of specific strength (ratio of strength to weight), which is especially advantageous for use as an implant. In contrast to solid materials or foams, fibers in different directions have different stress-related characteristics. No increase in strength can be ascertained in the fiber composite materials in the case of stresses that are perpendicular to the fiber; a significant amount of strength can be achieved, in contrast, in the case of stresses in the direction of the fiber. It is therefore possible to provide fiber composite materials that have reinforcement elements at precisely the spots where they are required to absorb targeted stresses. The three-dimensional fiber structure made up of reinforcing metallic fibers added to the mineral bone cement is, accordingly, a fiber structure with a three-dimensional design that assumes a framework-providing function; the reinforcement elements are aligned in such a way that the are adapted to the stresses of the bone. In the process, the textile structures are adapted to the three-dimensional contour of the implants in a dimensionally stable way.

A fiber structure providing a framework is, in the sense of the invention, a three-dimensional fiber structure that preforms the contour of the implant and that has a fiber structure aligned in such a way that it is adapted to the stresses of the implant for the defective area of the bone or joint that is to be repaired.

The fiber structure represents an at least partially three-dimensional portrayal of the implant for the defective area of the bone to be repaired to make an authentic or nearly authentic reconstruction of a defective area possible.

As examples, the following can therefore be created with the implants as per the invention:
 Augmentation materials in the form of cylindrical implants for femur fractures or in the form of intervertebral implants for spinal fusions and vertebral body replacement implants.
 Augmentation materials for the tibial plateau for a knee revision
 Plate-shaped elements, for instance for shoulder-blade fractures, skull fractures or pelvic fractures FIG. 5 show an augmentation material for the tibial plateau for a knee revision. The augmentation material shown in FIG. 5 is a conically formed, cylindrically shaped part with a recess. A multilayer, conically formed, cylindrically shaped fiber structure made of long metallic fibers and/or endless metallic fibers, providing a framework, that is embedded in the bone cement matrix is in the interior.

Because of the diversity of structures that can possibly be formed by metallic fibers, implants of any arbitrary dimensions and shapes can be created. It is advantageously possible to create graded implants or implant materials in the form of fiber composite materials that have reinforcements in the desired places (for instance for the fastening of an implant to the bone) and/or have porous areas in other places (for instance for bone tissue to grown in). In particular, it is possible to place the reinforcing fibers in the fiber composite material in the places where especially high tensile forces could occur. The characteristics of the matrix and of the reinforcing metallic fibers can be optimally used in this way by having the matrix, which can handle pressure especially well, serve as an abutment for the metallic fibers and fiber preforms containing metallic fibers that can be subjected to especially strong tensile forces. The metallic fibers are therefore preferably concentrated in the outer area in the case of cylindrical implants. In the case of flat implants, the metallic fibers are preferably on both outside areas. Alternatively, the reinforcement with metallic fibers can be limited to one side in the case of a foreseeable direction of stress from one side.

Long metallic fibers and/or endless metallic fibers that are preferably in the form of a fiber preform are used for the invention. Long fibers are understood to mean fibers with a length of 5 mm-50 mm. Endless fibers are understood to mean fibers with a length of more than 50 mm. Fibers with a length of at least 10 mm are preferably used with a further preference for at least 30 mm and an especial preference for endless fibers. As a preference, the fibers have an aspect ratio (ratio of length to diameter of the fibers) of at least 10:1, preferably at least 20:1, especially preferably at least 100:1. Especially good reinforcement is achieved in an implant as per the invention via an aspect ratio that is as large as possible.

The long metallic fibers and/or endless metallic fibers that are used can have an arbitrarily shaped cross-sectional area. The diameter of the fibers is preferably a maximum of 3 mm here, a maximum of 1 mm as a preference, with a special preference for a maximum of 0.5 mm.

The following embodiments are preferred for the invention:

In a preferred embodiment of the invention, the fiber structures in the implant providing a framework are aligned in preferential directions and/or are concentrated in the outer area of the implant as per the invention. It can consequently be ensured that targeted stresses in the form of tensile forces, compressive forces and/or bending forces will be borne in an advantageous way.

In one embodiment of the invention, the fiber structures providing a framework exist in the form of multifilaments and/or as a fiber preform with at least one layer.

Scrims, braids or fleeces can be comprised of at least one layer of a scrim, braid or fleece here. Multi-layer fiber structures produced in a textile fashion are preferred, especially preforms made of multi-layer textile fabrics, scrims or braids with at least 2 layers; additional filler yarn is appropriate in the main stress direction. A higher density of metallic fibers is advantageously achieved in the graded implant due to the multi-layer arrangement of fiber structures produced in a textile fashion. A local or comprehensive reinforcement of an implant as per the invention is thus enabled via the targeted placement and distribution of the fiber structures produced in a textile fashion.

When individual fiber filaments or fiber preforms are used, the metallic fibers are in the form of long multi-filaments in one embodiment of the invention, preferably throw or braided or in the form of threads or cords. Fiber composite materials with high bending strength in the direction of the fibers can be produced because of that. Individual fibers or fiber bundles in the form of filler yarn are suitable here for increasing the bending and torsion resistance as a special preference.

Fiber structures have pores with a size of 100-2500 μm between the metallic fibers in one embodiment as per the invention.

There are preferably more than 80% by weight of the metallic fibers within a range of 0.1-5 mm measured from the outside of the implant.

The metallic fibers can be in the form of individual fibers (monofilaments) or fiber bundles (multi-filaments) or in the form of fiber structures produced from that (such as cords or ropes) or in the form of a fiber preform for processing in an implant as per the invention. The form of a fiber preform is preferred due to the simpler handling. The individual fibers, preferably via textile-type processes (such as weaving, knitting or braiding), are put together into a preform with regard to that. Preferably forms of fiber preforms are textile fabrics, scrims (including multi-axial scrims), knitted fabrics, braids or fleeces. Endless fibers are interwoven in textile fabrics as a preference. The fibers in scrims, preferably endless fibers, are parallel and extended and held together via stitching. If the fibers are not exclusively oriented in the plane, this is a multi-axial scrim. Especially preferred fiber preforms have pores with a size of 100-2500 μm (maximum distance between two neighboring fibers) between the metallic-fiber filaments. A fiber preform containing a set as per the invention and a fiber preform used in a process as per the invention are preferably in one of the above-mentioned forms. The three-dimensional shape of a fiber preform is adapted to the defective area of the bone as a preference. Cylindrical or plate-shaped fiber preforms are preferred; it is preferred that the metallic fibers are arranged in the outer areas of the cylinder or the plate. More than 80% by weight of the metallic fibers are preferably within a range of 0.1-5 mm measured from the outside of the implant as per the invention. The long metallic fibers and/or endless fibers in the fiber composite material can be aligned in different ways when individual filaments of the fibers are used. In one embodiment, the long metallic fibers and/or endless fibers in the fiber composite material are randomly distributed and aligned. The fiber composite materials in that case can be stressed in the same way in any direction. In another embodiment, the long metallic fibers and/or endless fibers in the fiber composite material are aligned in preferential directions; in so doing, the individual fibers are essentially parallel to one another. It is possible in that case to increase the bending strength of the fiber composite materials that are obtained in selected directions (namely along the alignment of the fibers).

The implant represents a complete or at least partial three-dimensional portrayal of the defective area of the bone to be repaired in order to make an authentic or nearly authentic reconstruction of the defect area possible. It can be ensured that the implant can take over the lacking function of the defective bone area in part or in whole because of that.

Fiber structures made of metallic fibers produce in a textile fashion, which are suitable for producing implants of any arbitrary dimensions and shape due to their diversity, are therefore advantageously suitable for a reconstruction of the defective area of the bone. An authentic reconstruction of the defective area of the bone can consequently take place based on the individual patient with the implant as per the invention.

Experience has shown that fiber structures in a cylindrical shape that provide a framework can be used, as an example, for the production of standardized intervertebral implants (to be used for spinal revisions) or as an augmentation material for the tibial plateau (to be used for knee revisions). Fiber structures providing a framework for plate-shaped implants can be used, for instance, in revision elements for fractures in the shoulder area or in the pelvic area or in the case of skull fractures.

Metallic fibers could be exclusively used in fiber composite materials as per the invention; other fibers could also be included as an option. The other fibers are preferably fibers from one or more polymers, preferably from one or more resorbable polymers.

Both metals that are not decomposed in the body (non-resorbable metals) and metals that corrode in the body and that are successively decomposed in the body in the process (resorbable metals) are suitable as metals for implants as per the invention.

The metallic fibers are comprised of a non-resorbable metal in one embodiment of the invention, preferably selected from titanium, tantalum, niobium, gold, silver, cobalt, rhenium, hafnium, alloys containing the above-mentioned metals (preferably with at least 60% by weight) and stainless steel alloys. Titanium, titanium alloys or stainless steel alloys are preferred among them; titanium or titanium allows are especially preferred.

In a further embodiment of the invention, the metallic fibers are comprised of a resorbable metal (also called bio-corrodible here), preferably selected from pure iron, zinc, magnesium, base iron alloys, zinc alloys or magnesium alloys. Among them, pure iron, base alloys of iron, magnesium or magnesium alloys are preferred; magnesium or magnesium alloys are especially preferred.

In a further embodiment of the invention, metallic fibers (resorbable metal fibers and non-resorbable metal fibers, as described above, are equally suitable for this) are used that have a metallic coating (with a further metal that is not identical to the metal of the fiber core) or a coating with a non-metallic, bio-compatible material. The bio-compatibility of the metallic fibers is advantageously increased by the coating. Preferred metals for the coating are titanium, titanium alloys (preferably Ti6Al4V, Ti5Al4Nb, Ti5Al2.5Fe or nitinol), stainless steel alloys, cobalt-based alloys and tantalum, niobium, molybdenum, rhenium, hafnium and their alloys. Among them, titanium, titanium alloys, stainless steel alloys or cobalt-based alloys are especially preferred. Preferable non-metallic, bio-compatible materials for the coating are preferentially selected from calcium phosphates, magnesium phosphates, magnesium oxide, titanium dioxide and/or titanium nitride (preferably titanium dioxide and/or titanium nitride).

The surface of the metallic fibers is preferably treated to achieve better adhesion between the metallic fibers and the matrix material, and thus the mineral bone cement, in the fiber composite materials. The surface of the metallic fibers is preferably roughened, silicate-coated, phosphatized, eloxadized or anodized. Better stress transfer is advantageously achieved between the materials of the fiber composite material because of that.

The compressive strength of an implant as per the invention is preferably >50 MPa, with a further preference for >80 MPa. The bending strength (4-point bending strength) of an implant as per the invention is preferably >10 MPa, preferably >15 MPa. The tensile strength of an implant as per the invention is preferably >10 MPa.

Maximum bending strengths of approx. 85-95 MPa were achieved with the implants as per the invention, which contained braid types reinforced with multiple layers and/or with filler yarn.

The mineral bone cement, especially the mineral bone cement powder, preferably contains silicates, phosphates, sulfates, carbonates, oxides and/or hydroxides in association with calcium ions, magnesium ions, and/or strontium ions. Among those, Calcium phosphates and/or magnesium phosphates are preferred. The mineral bone cement preferably contains calcium and/or magnesium sales of orthophosphoric acid, of dimeric or polymeric phosphoric acid, glycerophosphoric acid, and other mono or disubstituted organic phosphoric acid esters; calcium and/or magnesium salts of orthophosphoric acid are especially preferred. As a special preference, the mineral bone cement contains at least one of the following compounds: monocalcium phosphate monohydrate, calcium monophosphate anhydrite, dicalcium phosphate anhydrite, dicalcium phosphate dihydrate, octacalcium phosphate, a tricalcium phosphate, β tricalcium phosphate, amorphous calcium phosphate, hydroxyapatite, calcium-deficient hydroxyapatite, substituted hydroxyapatite, non-stoichiometric hydroxyapatite, nano-hydroxylapatite, tetracalcium phosphate, calcium sulfate, calcium sulfate hemihydrate, calcium sulphate dihydrate, calcium oxide, calcium hydroxide, calcium carbonate, calcium glycerophosphate, calcium citrate, calcium lactate, calcium acetate, calcium tartrate, calcium chloride, calcium silicate, magnesium hydrogen phosphate, trimagnesium phosphate, magnesium dihydrogen phosphate, magnesium chloride, magnesium glycerophosphate, magnesium hydroxide, magnesium hydroxide carbonate, magnesium oxide (MgO), magnesium citrate, calcium-magnesium carbonate (dolomite), magnesium silicates.

The mineral bone cement powder can exclusively consist of mineral components. As an option, the mineral bone cement power contains resorbable polymeric additives, preferably selected from chitosan, hyaluronic acid, gelatins, chondroitin sulfate, cellulose derivatives, starch derivatives, alginate, water-soluble acrylates, polyethylene glycol, polyethylene oxide, polyvinylpyrrolidone, and copolymers made of water-soluble acrylates with polyethylene glycol and/or polyethylene oxide.

In one embodiment of the invention, the mineral bone cement powder exists in the form of a powdery solid before the hardening reaction is triggered. To trigger the hardening action, the mineral bone cement powder is mixed with water or an aqueous solution to form a pasty preparation with which the long metallic fibers and/or endless fibers that preferably exist in the form of a fiber preform are impregnated to produce the implant as per the invention.

An implant as per the invention can preferably be obtained via the impregnation of a fiber preform that contains long metallic fibers and/or endless metallic fibers or that consists of them with a pasty preparation that contains resorbable mineral bone cement powder dispersed in a liquid.

In a preferred embodiment of the invention, the mineral bone cement powder exists in the form of a water-free preparation that contains the mineral bone cement powder dispersed in a non-aqueous and water-free carrier fluid before the triggering of the hardening reaction. The water-free preparation exists in a pasty form. The long metallic fibers and/or endless fibers that preferably exist in the form of a fiber preform are impregnated with the water-free preparation to produce the implant as per the invention (preferred variant). As an alternative to that, the long metallic fibers and/or the endless fibers that preferably exist in the form of a fiber preform are impregnated with the water-free preparation, which was previously put in contact or mixed with water or an aqueous solution, to produce the implant as per the invention.

Suitable water-free, pasty preparations preferably have, in the sense of the invention, a viscosity between 0.1 and 350,000 mPa and, in particular, a viscosity not greater than 200,000 mPa at room temperature.

The viscosity of the cement pastes can be influenced via the adjustment of the distribution of particles sizes with the same powder/liquid ratio. Cement powders with coarse particles have a lower viscosity after being mixed, but the also have lower strengths after hardening. The cements are therefore prepared in such a way that the characteristics are adapted to a desired viscosity. Cement powders with a broad distribution of particle sizes, in which a range of <1 µm to >50 µm is covered, are especially advantageous. Powder preparations in which >20% of the powder mass has a particle size of <5 µm, >20% of the powder mass has a particle size of 10-50 µm and >10% of the powder mass has a particle size of >50 µm are especially preferred.

Cements that enable a good filling of dense wire structures and that provide good mechanical strengths are advantageously obtained by setting the particle sizes of the mineral bone cement powder to a medium range of approx. 8 µm, by setting the distribution of particles sizes at <1 µm to >50 µm and by setting the powder-liquid ratio during the cement mixing to l/p 0.5. Moreover, the cement mixtures that are obtained have compressive strengths of up to 100 MPa.

In a preferred embodiment of the invention, the implant as per the invention is comprised of long metallic fibers and/or endless metallic fibers in combination with a water-free preparation in the form of a paste in which mineral bone cement powder is dispersed in a water-free and non-aqueous, preferably an organic, carrier fluid. Without contact with water, the mineral cement powder does not react to become a solid that does not easily dissolve in this application, so the implant in this form can be flexibly shaped, it is easy to handle and it can be adapted in a simple way to the defective bone area to be treated. In the process, it is advantageously possible to use the implant for implantation immediately without prior hardening of the mineral bone cement existing in the form of a pasty preparation. In that case, the mineral bone cement hardens in the body via contact with bodily fluids to form the solid that does not easily dissolve. An adequate support effect already exists at the point in time of the implantation, however, because of the reinforcement with the metallic fibers. Alternatively, the possibility exists to already have the mineral bone cement powder hardened before the implantation via contact with water or an aqueous solution.

Water-free in the sense of the invention is understood to mean a proportion of less than 1% by weight of water, preferably less than 0.1% by weight of water. The carrier fluid is preferably an organic carrier fluid in which the mineral bone cement powder is dispersed. The organic carrier fluid is chosen in such a way that it does not react itself with the mineral bone cement powder. Basically, both carrier fluids that are soluble in water and carrier fluids that do not easily dissolve in water are suitable. Not easily dissolving in water in the sense of the invention is understood to mean that its maximum solubility in water is 1.0 mol/l, preferably 0.1 mol/l. Compounds with a maximum solubility in water of more than 1 mol/l (preferably more than 3 mol/l) are designated as water-soluble here. Carrier fluids that do not easily dissolve in water are preferred, however. Hydrophobic carrier fluids are especially preferred. The carrier fluid contained in the water-free preparation is preferably bio-compatible. The proportion of the carrier fluid with respect to the total mass of the water-free preparation is preferably 5 to 25% by weight, with a further preference for 5 to 20% by weight, preferably 5 to 15% by weight, preferably 5 to 12.5% by weight.

Preferred carrier fluids that do not easily dissolve in water and that are contained in the water-free preparation are selected from glycerol triacetate, glycerol tributyrate, glycerol trioleate, glycerol dioleate, glycerol monooleate, caprylocaprate, decyl oleate, isopropyl myristate, isopropyl palmitate, oleic acid, oleyl alcohol, oleyl oleate, short-chain triglycerides, medium-chain triglycerides, short and medium-chain fatty acid esters of propylene glycol, ethyl benzoylacetate, ethyl butyrate, ethyl butyrylacetate, ethyl oleate, ethyl caproate, ethyl caprylate, ethyl caprate, ethyl laurate, ethyl laevulinate, ethyl myristate, ethyl palmitate, ethyl linoleate, ethyl stearate, ricinoleic acid, linoleic acid, linolenic acid, arachidic acid, oleic acid, ethyl arachidate, α-tocopherol, β-tocopherol, γ-tocopherol, δ-tocopherol, benzyl alcohol, benzyl benzoate, diethyl butylmalonate, diethylene glycol dibutyl ether, diethyl ethylmalonate, diethyl phenylmalonate, diethyl phthalate, diethyl sebaceate, diethyl suberate, diethyl succinate, dibutyl maleinate, dibutyl phthalate, lecithin, paraffin oil, petrolatum, liquid paraffins and esters of sebacic acid. Short or medium-chain triglycerides or medium-chain fatty acid esters of ethylene glycol and propylene glycol are especially preferred carrier fluids. Short-chain fatty acid compounds are understood to mean compounds of fatty acids with a length of 2 to 5 carbon atoms in each case. Medium-chain fatty acid compounds are understood to mean compounds of fatty acids with a length of 6 to 14 carbon atoms in each case. Especially preferred carrier fluids that do not easily dissolve in water and that are contained in the water-free, pasty preparation are selected from esters of fatty acids and monohydric and polyhydric alcohols. Among them, triglycerides are preferred. Among them, esters of triglycerides with fatty acids that have less than 14 C atoms on average are a very special preference. Carrier fluids that do not easily dissolve in water that are a further preference are polypropylene glycols and esters of polypropylene glycols, as well as monoethers and diethers of polypropylene glycols with monoalcohols.

Preferred water-soluble carrier fluids that are contained in the water-free preparation are selected from polymers of ethylene glycol, short-chain oligomers of propylene glycol, copolymers with ethylene glycol and propylene glycol units, mono and dimethyl ethers of polyethylene glycol, glycerol and their water-soluble ethers and esters and diglycerol and polyglycerol.

Preferably surfactants, with a further preference for at least one non-ionic surfactant, with a special preference for at least one anionic and at least one non-ionic surfactant, are further components of the water-free preparation. The weight ratio of the total solids contained in the water-free, pasty preparation to the sum of the weights of the organic carrier fluid and the surfactants is preferably more than 5 here, with a further preference for more than 6 and a special preference for more than 10. This has the advantage that the mineral bone cement matrix has especially high compressive strength after the hardening.

A further component of the mineral bone cement, preferably of the water-free preparation, is at least one setting accelerator as a preference. The setting time and the course of the pH value during the hardening of the preparation as per the invention will be adjusted by that. Phosphate salts, organic acids or salts of organic acids are preferred setting accelerators. Phosphates containing sodium and/or potassium ions or salts of organic acids containing sodium and/or potassium ions are preferred. Phosphates containing potassium ions (preferably potassium phosphates, especially potassium dihydrogenphosphate and dipotassium hydrogenphosphate) are a special preference. Especially advantageous setting kinetics, especially in combination with non-ionic surfactants (particularly well in combination with non-ionic and anionic surfactants), are achieved with phosphates containing potassium. The water-free, pasty preparation will preferably contain the setting accelerator in a proportion (with reference to the mass of the mineral cement powder) of 0.1 to 5%, with a special preference for 0.2 to 4%, and a very special preference for 0.5 to 3.5%.

In one embodiment of the invention, the water-free preparation contains surfactants and/or a setting accelerator and/or water-soluble fillers.

Active ingredients are further preferred components of the mineral bone cement. Active pharmaceutical ingredients with a growth-stimulating or antimicrobial effect are preferred. Especially preferred active ingredients are selected from antibiotics, antiseptics, antimicrobial peptides, antiresorptive agents (preferably bisphosphonates, corticoids, fluorides, proton pump inhibitors), bone-growth-stimulating substances (preferably growth factors, vitamins, hormones, morphogens, preferably bone morphogenetic proteins among them). The implant as per the invention is especially well suited to being an agent carrier. This is because, on the one hand, the implant as per the invention is prepared at low temperatures (preferably under 50° C.). This permits temperature-sensitive ingredients to be worked in without problems. On the other hand, the implant as per the invention offers improved active-ingredient delivery, because the active ingredients are successively released via the resorption of the mineral bone cement. The implant as per the invention therefore allows a controlled release of the active ingredient and is suitable in an especially advantageous way for the use of temperature-sensitive substances.

Further preferred components of the mineral bone cement, preferably of the water-free preparation, are fillers. Water-soluble, particulate fillers made of mineral or organic substances are preferred. The porosity of the solid formed during hardening with water can be advantageously adjusted by the use of water-soluble particles. Water-soluble fillers preferably have a particle size of 50 µm to 2000 µm, and from 100 µm to 1000 µm as a further preference. The water-free preparation preferably contains water-soluble fillers in a proportion of 5 to 90% by volume, with a further preference for 10 to 80% by volume (with reference to the total volume of the water-free preparation). Preferred water-soluble fillers are selected from sugars (preferably sucrose), sugar alcohols (preferably sorbitol, xylitol, mannitol), and water-soluble salts (preferably sodium chloride, sodium carbonate or calcium chloride). The water-soluble fillers are preferably used in the form of granules. The proportion of pores of the hardened mineral bone cement is preferably 10 to 75% by volume, with a special preference for 10 to 50% by volume. The pores preferably have a mean pore width (maximum inner extension of a pore) of 100-2500 µm, with a special preference for 100-1000 µm.

As a special preference, all of the components of the mineral bone cement can be resorbed in the body. The combination of resorbable metallic fibers and the resorbable mineral bone cement is especially preferred for the invention.

The proportion of metallic fibers vis-a-vis the total fiber composite material is preferably 1-90% by weight, with a further preference of 5-75% by weight, an especial preference of 10-75% by weight, and a very special preference of 25-75% by weight in an implant as per the invention.

The invention also comprises a method for manufacturing an implant as per the invention, preferably of a bone implant that contains or that is comprised of an implant of that type. The method is comprised of the provision of the fiber composite material with the steps:

Provision of a pasty preparation that contains resorbable mineral bone cement powder dispersed in a liquid, preferably water, an aqueous solution or a non-aqueous and water-free carrier fluid, and Impregnation of several long metallic fibers and/or endless metallic fibers with an aspect ratio of at least 100:1 in the form of fiber structures with the pasty preparation providing a framework; the metallic fibers preferably exist in the form of a fiber preform, preferably completely metallic, which contains the long metallic fibers or endless metallic fibers.

In the first step of the method as per the invention, a pasty preparation is provided with a mineral bone cement powder. Mineral bone cement powder is dispersed in water or an aqueous solution for that in one embodiment of the method, so a hardening bone cement preparation in a pasty form can be obtained. The metallic fibers, preferably the fiber preform, is subsequently impregnated with this preparation.

In another embodiment of the method, mineral bone cement powder is dispersed in a water-free carrier fluid, so a water-free preparation in a pasty form can be obtained. The water-free preparation in one design variant is put into contact or mixed with water or an aqueous solution; the hardening reaction of the bone cement is triggered because of that. After that, the metallic fibers, preferably the fiber preform, is impregnated with this hardening but still pasty preparation. In another, especially preferred design form, the metallic fibers, preferably the fiber preform, are impregnated with the water-free preparation without it having come in contact beforehand with water or an aqueous solution. The result of this latter process is a moldable implant made of a flexible fiber composite material that can be directly implanted and that successively hardens into a solid solely because of the presence of body fluid.

The fiber preform is preferably impregnated with the pasty preparation under increased pressure, preferably in a range of more than 1 to 100 MPa. This has the advantage that a nearly pore-free bone cement matrix can be obtained and that especially high compressive strengths can be achieved because of that. This is preferably managed by putting the fiber preform into a mold, and the pasty preparation is filled into the pore system of the metallic preform at first without additional applied pressure (this is preferably supported by shaking or vibration). After that, the mold is closed and pressurized with a pressure of up to 100 MPa. The volume of air bubbles remaining in the bone cement can be reduced to $\frac{1}{1000}$ in this way (compared to the filling of the fiber preform without pressurization).

According to an advantageous embodiment of the method as per the invention, the fiber preform is put into a casting mold and a pasty preparation is filed into the pore system of the metallic preform with mechanical movement; the fiber structure providing a framework is surrounded by the pasty mass. The process that was described is preferably supported by shaking or vibration; gases (e.g. air or inert gases) are driven out of the molded part at the same time.

In the case of a pasty preparation containing water, the pasty preparation hardens after coming into contact with the fiber structures providing a framework. Depending on the desired shape and surface structure of the implant as per the invention, it can be pressed into a specific shape before the hardening.

A complete wetting of all of the wires is to specifically be ensured via pressurization in the case of more dense, multi-layer fiber structures that provide a framework (e.g. 3× or 4× braid). After the application and distribution of the cement in the entire sample, a cement mixture that is runny enough can still flow well between the tight-meshed or porous fiber structure that provides a framework.

No ceramic sintering is done for the hardening, even in the case that the hardening of the mineral bone cement takes place before the implantation. The hardening is therefore preferably done at a temperature below 250° C., below 100° C. as a special preference and below 50° C. as a further preference.

Furthermore, a filled fiber structure providing a framework can be put into a defined three-dimensional shape, e.g. pressing a cylindrical structure into a plate, via external shaping processes before the hardening.

The implant as per the invention can already be used alone as a bone implant, or it can be put together into a combination with further elements that are customary in bone implantation to form a complex bone implant. In one preferred embodiment, the bone implant is preferably comprised of only the implant as per the invention in part. Any other formed parts, preferably metallic, can be contained in the bone implant as per the invention here, firmly joined with the implant, in addition to the implant as per the invention. The corresponding formed parts and joining possibilities are known from the prior art. In a preferred case, the bone implant is comprised of a plate (preferably metallic) or a nail (preferably metallic); the plate or the nail is fastened to the bone via metallic screws in each case. Bone-joint implants are likewise preferred; the side turned towards the bone is comprised of the implant as per the invention or contains an implant as per the invention, and the side turned towards the joint is comprised of a solid metal or a solid ceramic. Examples of that are combined acetabulums that include components from knee prostheses and the resurfacing of femoral heads.

The invention therefore also includes a bone implant that is comprised of at least one implant as per the invention or that contains at least one implant as per the invention in combination with a component made of solid metal or made of a solid ceramic.

The invention also includes a set for manufacturing an implant as per the invention, preferably of a bone implant, that contains an implant or that type or that is comprised of an implant of that type. The set includes the following components:

a) At least one bone cement preparation, comprising resorbable mineral bone cement powder, b) Several long metallic fibers and/or endless fibers in the form of a fiber structure providing a framework (preferably completely metallic), preferably a fiber preform.

The bone cement preparation of a set as per the invention preferably exists in a ready-made fashion as follows:

Single-component system:
  Mineral bone cement powder or
  Mineral bone cement powder dispersed in a preferably organic carrier fluid (water-free preparation); or
Two-component system with separately packaged components in each case:
  Mineral bone cement powder and water or an aqueous solution,
  Mineral bone cement powder dispersed in a preferably organic carrier fluid (water-free preparation) and water or an aqueous solution (preparation containing water); as an option, particulate solids that do not react with water to form a solid are dispersed in the aqueous solution, so the aqueous solution takes on the form of a paste.

As a special preference, the bone cement preparation is in the form of a water-free preparation in a set as per the invention (single-component system, which is a very specially preferred variant) or in the form of a water-free preparation in combination with a preparation containing water (two-component system). There is a special preference in this case for the bone cement preparation to at least be put into a waterproof packaging.

Furthermore, the invention includes the use of an implant as per the invention or a bone implant as per the invention for treating a bone defect. A preferred application area is osteosynthesis. A high level of bioactivity of the implant is desired in this area; removal of material after the fracture heals is to be avoided, however. The invention also includes the use of a set as per the invention for producing a bone implant.

BRIEF DESCRIPTION OF THE DRAWINGS

The invention is to be explained in more detail below with the aid of the following figures and examples without limiting the invention to them.

DETAILED DESCRIPTION OF THE PREFERRED EMBODIMENTS

Example 1

Bond Strength of a Composite Material of Magnesium-Calcium Phosphate Cement with a Titanium Wire Magnesium-calcium phosphate cement with the composition $Mg_{2.5}Ca_{0.5}(PO_4)_2$ is obtained via sintering (5 h at 1050° C.) and a subsequent grinding of calcium and magnesium phosphates and carbonates in a molar ratio to the end composition. The Following components were used: 0.33 mol $CaHPO_4$, 0.17 mol $CaCO_3$, 1.67 mol $MgHPO_4*3\ H_2O$ and 0.83 mol $Mg(OH)_2$. The bone cement powder that was obtained in this way was mixed with an aqueous 3.5 mol/l ammonium phosphate solution in a ratio of 0.5 (mass of the liquid to the mass of the bone cement powder). A titanium wire of the alloy Ti6Al4V with a diameter of 0.5 mm and a length of 5 mm was cemented into the hardening compound. After 72 hours of incubation in a physiological salt solution at 37° C., the wire was pulled out of the cement body with a universal testing machine.

Figure 1:
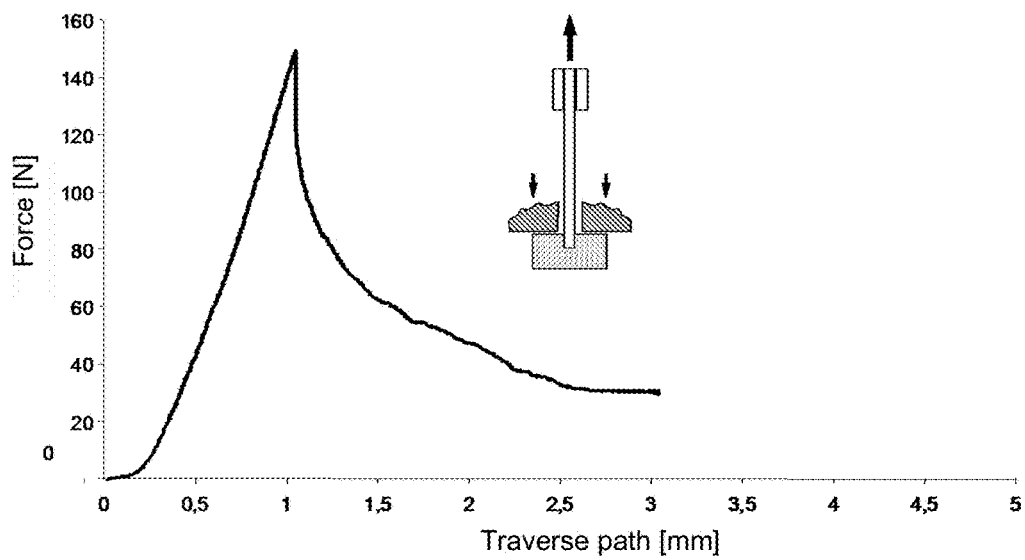
FIG. 1 Force-path diagram, pulling a titanium wire out of hardened magnesium-calcium phosphate cement FIG. 2 Force-path diagram, 4-point bending, implant as per the invention (pure titanium fiber scrim and magnesium-calcium phosphate cement) and reference sample (non-reinforced magnesium-calcium phosphate cement)

FIG. 1 shows the force-path diagram when the wire is pulled out of the cement matrix. The course of the force initially experienced a phase with a high loading to a maximum value of up to 150 N. A residual force of approx. 40 N to 20 N remained over a further pull-out path of 2 mm when the maximum load was exceeded, which shows that a catastrophic failure of a composite material as per the invention is not to be expected even when loads are exceeded; instead there is considerable fracture resistance. It is expected that this behavior will be more pronounced the more fibers there are in parallel with the direction of stress. The absolute value for the pull-out force of the wire out of the cement matrix shows an unexpectedly high adhesive strength of the titanium wire in the cement matrix, both with regard to the adhesive friction and the sliding friction.

Example 2

Bending Strength of an Implant as Per the Invention with Magnesium-Calcium Phosphate Cement and a Braid Made of Stainless Steel Wires in the Form of a Fiber Composite Material A braid of endless fibers made of stainless steel (fiber diameter 0.2 mm) was impregnated with magnesium-calcium phosphate cement of the composition in accordance with example 1. The proportion of the metallic braid vis-a-vis the fiber composite material was 3% by weight.

An increase in the tensile strength to 320% and an increase in the bending strength to 180% were already achieved with this small proportion. The best values were achieved with the variants reinforced with filler yarn.

|  | Tensile strength [MPa] | Bending strength [MPa] |
|---|---|---|
| Magnesium-calcium phosphate cement | 3.13 | 5.9 |
| Implant with Magnesium-calcium phosphate cement and stainless steel braid | 10.1 | 10.8 |
| Implant with magnesium-calcium phosphate cement and 1x-stainless steel braid with filler yarn | 13.5 | 8.37 |

The tensile strength were determined according to DIN EN ISO 527 Parts 1 and 5. The 4-point bending strength was according to DIN EN ISO 14125.

Example 3

Mechanical Characteristics of an Implant as Per the Invention with Calcium Phosphate Cement and Individual Fiber Filaments Made of Stainless Steel in the Form of a Fiber Composite Material During Hardening Under Normal Pressure Calcium phosphate cement of the composition 60% by weight of tricalcium phosphate, 26% by weight of dicalcium phosphate anhydrite, 10% by weight of $CaCO_3$ and 4% by weight of hydroxyapatite was kneaded together with a 1% by weight aqueous $Na_2HPO_4$ solution in the ratio of 0.4 ml solution to each gram of cement in the form of a water-free preparation; 30% by weight (with reference to the overall mass of the preparation) of stainless steel fibers (90 μm diameter, 100 mm length) were mixed in. The compound that was obtained in that was hardened in a silicone mold with the dimensions 6×6×100 mm³. After removal from the mold, the hardened molded part was incubated for 100 h at 37° C. in simulated body fluid and subsequently subjected to testing.

The compressive strength of the molded part is increased to 140% because of the fiber reinforcement.

|  | Compressive strength [MPa] |
|---|---|
| Calcium phosphate cement | 17.7 |
| Implant with calcium phosphate cement and stainless steel fibers | 24.9 |

The compressive strength was determined in accordance with DIN EN ISO 5833.

Example 4

Mechanical Characteristics of an Implant as Per the Invention with Calcium Phosphate Cement and Individual Fiber Filaments Made of Stainless Steel in the Form of a Fiber Composite Material During Hardening Under a Pressure of 100 MPa Stainless steel fibers and calcium phosphate cement were mixed into a pasty mass, analogously to Example 3, and put into silicone molds. After that, pressurization took place with the aid of a ram so that a pressure of 100 MPa was set. After one hour, the hardened molded part was removed from the mold, incubated for 100 h at 37° C. in simulated body fluid and subsequently subjected to testing.

The bending strength of the molded part that was obtained was significantly increase vis-a-vis the molded part that was hardened under normal pressure. A massive increase in the compressive strength to 200 MPa was noted in the molded part that was obtained.

Example 5

Mechanical Characteristics of an Implant as Per the Invention with Calcium Phosphate Cement and Individual Fiber Filaments Made of Stainless Steel in the Form of a Fiber Composite Material, Providing the Bone Cement in the Form of a Water-Free Preparation A water-free preparation made up of 84% by weight of the calcium phosphate cement, as described in Example 3, and 16% by weight of a mixture of Miglyol 812 (a saturated, partially synthetic, medium-chain triglyceride) and Tween 80 (97% by weight of Miglyol and 3% by weight of Tween 80) was created.

Stainless steel fibers, as described in Example 3, were added to the compound. The proportion of metal fibers to the preparation was 30% by weight.

A cord with a diameter of 8 mm was created in which the stainless steel fibers were largely arranged in parallel along the cord. The cord was pressed into an oblong mold with a cross-section of 6×6 mm and subsequently hardened by being laid in water. After the hardening, there was an incubation in simulated body fluid at 37° C. for 100 h.

Subsequently, the material was subjected to mechanical testing:

The mechanical testing shows a significantly greater bending strength for the reinforced material than was the case for the non-reinforced material.

Example 6

Mechanical Characteristics of an Implant as Per the Invention with Magnesium-Calcium Phosphate Cement and a Cylindrical Braid of Stainless-Steel Fibers in the Form of a Fiber Composite Material Magnesium-calcium phosphate cement is provided as described in Example 1 and mixed with an aqueous ammonium phosphate solution. The hardened cement paste was put into a cylinder whose wall was formed from a braid of stainless steel fibers (diameter of a fiber 0.2 mm). The cylinder had a diameter of 10 mm and a length of 100 mm.

The cylinder was completely filled with the cement paste until the cement paste escaped from the pores of the stainless-steel braid. The fiber composite material that was obtained in this way was hardened at 37° C. in simulated body fluid for 100 h.

The implant as per the invention had a 4-point bending strength of 50 MPa. A molded part with the same dimensions made of non-reinforced magnesium-calcium phosphate cement had a bending strength of <15 MPa. The unfilled cylinder of the metal braid had no bending strength. The 4-point bending strength was determined according to DIN EN ISO 5833.

Example 7

Mechanical Characteristics of an Implant as Per the Invention with Magnesium-Calcium Phosphate Cement and a Scrim Made of Titanium Wire in the Form of a Fiber Composite Material Magnesium-calcium phosphate cement is provided as described in Example 1 and mixed with an aqueous ammonium phosphate solution. The hardened cement paste was put into a scrim made of pure titanium fibers (fiber diameter 0.3 mm). Molded parts with the dimensions 80×10×6 mm³ were created from that. The proportion of metal in the molded parts was 1% by volume (corresponding to a proportion of 2% by weight). The molded parts were put into a physiological salt solution at 37° C. for 72 hours for hardening. The hardened molded parts were investigated in a universal testing machine for 4-point bending strength.

Compared to a non-reinforced molded part with the same dimensions made of magnesium-calcium phosphate cement, 20% more bending strength was found in the implant as per the invention at the point of cement failure (1st drop in stress).

Figure 2:
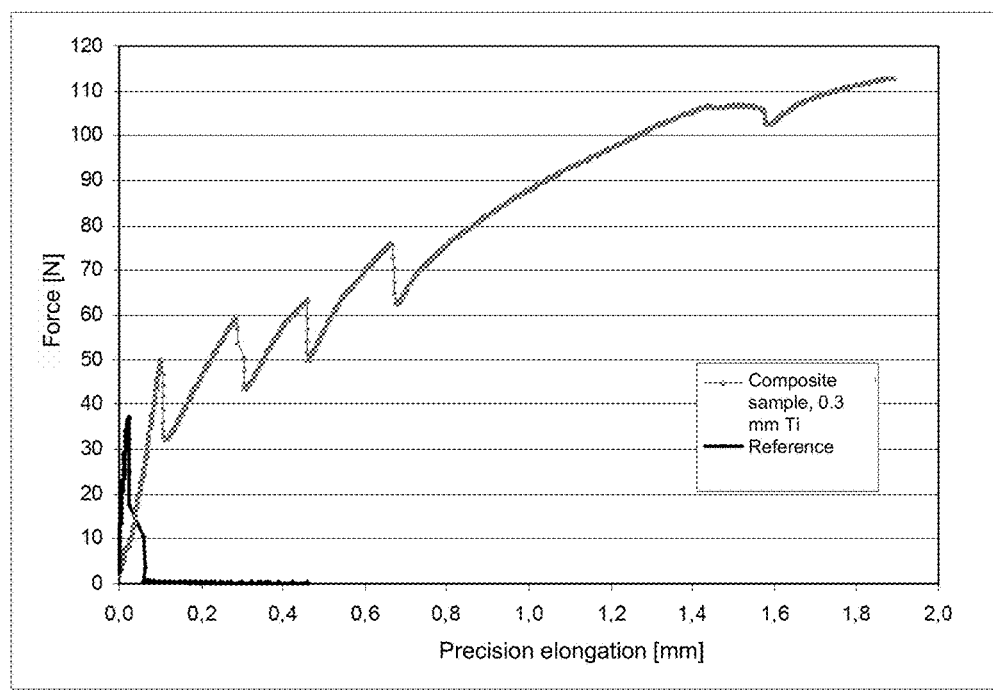

The non-reinforced molded part with the same dimensions made of magnesium-calcium phosphate cement (reference sample) completely fails when there is a low level of deformation. The implant as per the invention only shows a low drop in force, in contrast, and a continuous increase in force with further deformation (FIG. 2).

Example 8

Mechanical Characteristics of an Implant as Per the Invention with Magnesium-Calcium Phosphate Cement and a 2× Braid Made of Titanium Wire with Filler Yarn in the Form of a Fiber Composite Material Magnesium-calcium phosphate cement is provided as described in Example 1 and mixed with an aqueous ammonium phosphate solution. The hardened cement paste was put into a 2× braid made of pure titanium fibers (fiber diameter 0.3 mm). Molded parts with the dimensions 80×17×4 mm³ were created from that (the proportion of metal in the molded parts was 12% by weight). The molded parts were put into a physiological salt solution at 37° C. for 72 hours for hardening. The hardened molded parts were investigated in a universal testing machine for 4-point bending strength.

Compared to a non-reinforced molded part with the same dimensions made of magnesium-calcium phosphate cement (<20 MPa), bending strength that was more than 4 times higher was found in the implant as per the invention with an inserted 2× braid made of titanium wire with filler yarn (90 MPa). The implant as per the invention simultaneously shows a continuous increase in forced with sustained deformation (FIG. 3).

Figure 3:
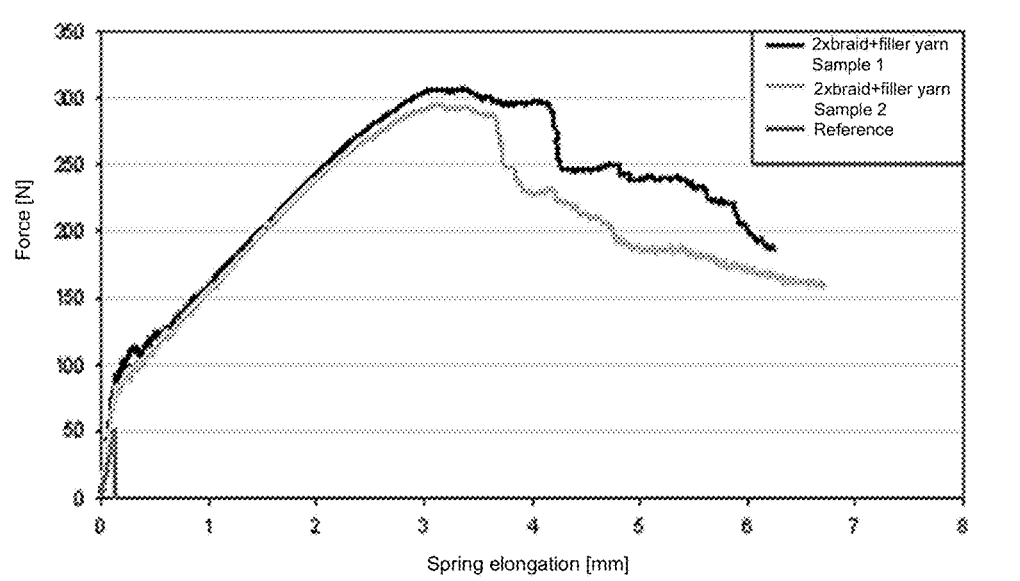
FIG. 3 Deformation curves of reference material and 2× braid+filler-yarn-reinforced plates during bending FIG. 4 (A) shows an untreated titanium braid that, in combination with a magnesium-calcium phosphate cement, represents fiber composite material (B) as per the invention; the braid containing metal is included in the magnesium-calcium phosphate cement.
Figure 4:
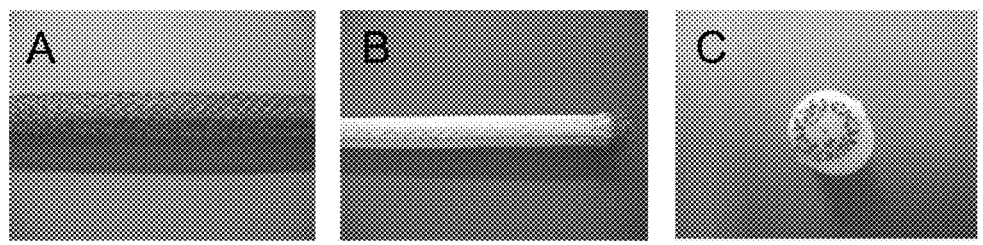
Figure 5:
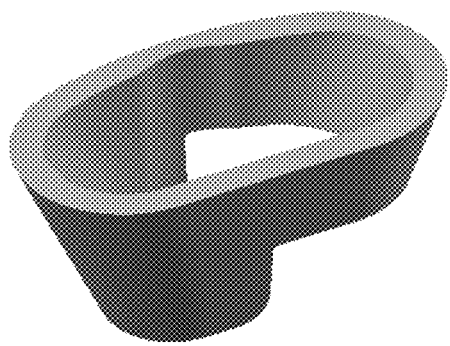
FIG. 5 Schematic portrayal of augmentation material for the tibial plateau for a knee revision.

FIG. 3 shows the course of the deformation curve under bending stress. It can clearly be seen here that a significantly greater amount of work is required to bring about deformation or failure of the composite samples than is the case with the brittle fracture of the reference.

Example 9

Comparison of the Bending Strength of an Implant as Per the Invention in the Form of Fiber Composite Materials Containing Magnesium-Calcium Phosphate Cement Combined with a Varying Number of Braids Made of Titanium The mechanical behavior of the composite materials was determined under the principal kind of stress, bending. Magnesium-calcium phosphate cement was provided for this, as described in Example 1, and mixed with an aqueous ammonium phosphate solution. The hardening cement paste was put into a scrim made of pure titanium fibers (fiber diameter 0.3 mm); the scrims have varying numbers of braids. Cylindrical molded parts with the dimensions l=100 mm, d=8 mm were created from that. The proportion of metal in the molded parts was 6 to 12% by weight, depending on the number of titanium braids. The molded parts were put into a physiological salt solution at 37° C. for 72 hours for hardening. The hardened molded parts were investigated in a universal testing machine for 4-point bending strength.

A significantly more positive influence of added filler yarn on the strength was shown in the bending tests of the cylindrical composite samples.

The tests (cf. the following table) show that the bending strength of magnesium-calcium phosphate cement can be increased by including titanium braids. The bending strength vis-a-vis a non-reinforced magnesium-calcium phosphate cement increases in the process with the number of included titanium braids of a 1×, 2× up to a 3× and 4× braid. The use of a 4× braid did not show an additional reinforcement effect here in comparison with a 3× braid.

| Sample | Bending strength [N] |
|---|---|
| Implant comprised of magnesium-calcium phosphate cement (reference) | 55.78 |
| Implant comprised of magnesium-calcium phosphate cement containing a 1x titanium braid | 212.00 |
| Implant comprised of magnesium-calcium phosphate cement containing a 2x titanium braid | 251.75 |
| Implant comprised of magnesium-calcium phosphate cement containing a 3x titanium braid | 375.33 |
| Implant comprised of magnesium-calcium phosphate cement containing a 4x titanium braid | 376.75 |

Example 10

Comparison of the Bending Strength of Implants as Per the Invention with a Braid Made of Titanium Wires and/or Filler Yarn in Combination with Different Cement Compositions of Magnesium-Calcium Phosphate Cement in the Form of a Fiber Composite Material Magnesium-calcium phosphate cement is provided as described in Example 1 and mixed with an aqueous ammonium phosphate solution. The hardening cement paste was put into a scrim made of pure titanium fibers (fiber diameter 0.3 mm); the scrims have varying numbers of braids and/or additional filler yarn. Molded parts with the dimensions 80×10×6 mm$^3$ were created from that (the proportion of metal in the molded parts was 6-12% by weight, depending on the type of scrim that was used). The molded parts were put into a physiological salt solution at 37° C. for 72 hours for hardening. The hardened molded parts were investigated in a universal testing machine for 4-point bending strength.

The bending strength increased to four times the amount because of the use of filler yarn in a 1× braid compared to braid material without filler yarn. The stress-strain diagrams of the bending tests show significant differences between a non-reinforced and a reinforced sample in the work required up to the failure of the materials.

Furthermore, the bending strengths were analogously determined vis-a-vis non-reinforced implants for selected scrim configurations with which an ideal strength increase was to be achieved with minimal wire content. The reinforcement effect of a 2× braid with filler yarn was compared with a 3× braid, in order to specifically investigate the influence of the material content and additionally contributed filler yarn on the mechanical characteristics of the composite material.

| Sample | Bending strength [N] |
|---|---|
| Implant comprised of magnesium-calcium phosphate cement (reference) | 72.88 |
| Implant comprised of magnesium-calcium phosphate cement containing a 2× titanium braid and filler yarn | 339.25 |
| Implant comprised of magnesium-calcium phosphate cement containing a 3× titanium braid | 332.00 |
| Implant comprised of a polymer PMMA cement | 190.00 |

The first fracture events in the cement occurred at around one-third of the maximum force; the further force effect was absorbed by the wire reinforcement until the samples completely failed. Maximum bending strengths of approx. 85-95 MPa were achieved with the two braid types; the mean values for the two reinforcement types are on a comparable level.

Example 11

Production of Molded Parts in the Form of Cylindrical and Plate-Shaped Components Containing Magnesium-Calcium Phosphate Cement A metal sample mold was prepared for the production of the cylindrical molded parts. It is comprised of two parts that are milled out in a half-round way and that can be firmly put together. The Ti braid that is used is firmly anchored to the ends and can be put under tension if necessary. Cylindrical molded parts with the dimensions L=200 mm, d=10 mm were produced in this sample mold.

The samples were prepared by means of an injection unit and cannula on a vibrator in the cylindrical form. Two-layer braids with filler yarn as the wire reinforcement were used. The diameter of the titanium-wire braid was chosen in an appropriate way for the shape (d=10 mm); in addition, the braid was dilated in the mold such that it made lateral contact with the wall. The cement filling took place from one open end by means of an injection unit and a long cannula with vibration.

After hardening over 4 days at 37° C., the ends of the sample were straightened out and burrs running lengthwise on both sides were ground off. The cement mixture was spread out very well over the entire length of 200 mm because of the vibration; very small air bubbles could merely be seen in the sample.

Plates with the dimensions 2.5×12×80 mm$^3$ made of composite material were produced as a further mold. Braids with a diameter of approx. 10 mm can be pressed to a size of approx. 80×12×2.5 mm$^3$ (L×W×H). The composite samples were produced from a two-layer braid+filler yarn. During the preparation, the Ti-wire braids were filled with MgCPC in a silicone hose with mechanical movement on a vibrator and subsequently pressed to form a flat sample by means of a hydraulic press. The sample production in a transparent hose material permits inspection of the cement distribution during the filling process. The samples were hardened over 4 days at 37° C.

Characteristic mechanical values of these osteosynthesis-plate components were determined by means of static and dynamic bending tests. All of the samples, which are reinforced with a 2× titanium braid and filler yarn, show an increase in the bending strength by around 400-500% compared with the non-reinforced references (cf. the following table).

| | Bending strength [MPa] | |
|---|---|---|
| Sample | Non-reinforced reference comprised of magnesium-calcium phosphate cement | Implant comprised of magnesium-calcium phosphate cement containing a 2× titanium braid and filler yarn |
| MgCPC-110523I/P 0.6 cylinder | 48 | 189 |
| MgCPC-120613I/P cylinder | 23 | 128 |
| MgCPC-120613I/P plate | 16 | 81 |
| MgCPC-120123C-04A plate | 15 | 78 |

The invention claimed is:

1. Implant made of a fiber composite material, containing:
   a) resorbable mineral bone cement as a matrix material,
   b) reinforcing, long metallic fibers and/or endless metallic fibers with an aspect ratio of at least 100:1 in the form of at least one fiber structure with a three-dimensional design providing a framework that preforms the contour of the implant, wherein said reinforcing, long metallic fibers and/or endless metallic fibers are arranged longitudinally with respect to the direction of stress to be applied to the implant and wherein stressed areas of the implant have a quantity of reinforcing, long metallic fibers and/or endless metallic fibers greater than the average quantity in the implant.

2. Implant according to claim 1, characterized in that the fiber structures providing a framework are concentrated in the outer area of the implant.

3. Implant according to claim 1, characterized in that the fiber structures providing a framework exist in the form of multifilaments and/or in the form of a fiber preform made of at least one layer.

4. Implant according to claim 3, characterized in that the fiber structures contain pores with a size of 100-2500 µm between the metallic fibers.

5. Implant according to claim 1, characterized in that more than 80% by weight of the metallic fibers are located in a range of 0.1-5 mm measured from the outside of the implant.

6. Implant according to claim 1, characterized in that the long metallic fibers and/or endless metallic fibers are made of a non-resorbable metal.

7. Implant according to claim 1, characterized in that the long metallic fibers and/or endless metallic fibers are made of a resorbable metal.

8. Implant according to claim 1, characterized in that the implant has a compressive strength of >50 MPa and/or a bending strength of >10 MPa.

9. Implant according to claim 1, characterized in that the mineral bone cement contains silicates, phosphates, sulfates, carbonates, oxides and/or hydroxides in combination with calcium ions, magnesium ions and/or strontium ions.

10. Implant according to claim 1, characterized in that the resorbable mineral bone cement exists in the form of a water-free, pasty preparation, wherein mineral bone cement powder is dispersed in a carrier fluid in the water-free, pasty preparation.

11. Implant according to claim 10, characterized in that the proportion of the carrier fluid with reference to the overall mass of the water-free, pasty preparation is 5 to 25% by weight.

12. Implant according to claim 10, characterized in that the water-free, pasty preparation contains surfactants and/or a setting accelerator and/or water-soluble fillers.

13. Implant according to claim 1, characterized in that the implant is reinforced with filler yarn.

14. Method for producing an implant in accordance with claim 1, comprising the provision of the fiber composite material with the steps:
   a) provision of a pasty preparation containing
      i. resorbable mineral bone cement powder,
      ii. that is dispersed in a liquid,
   b) impregnation of several long metallic fibers and/or endless metallic fibers with an aspect ratio of at least 100:1 in the form of fiber structures with the pasty preparation providing a framework.

15. Set for producing an implant according to claim 1, comprising the components:
   a) several long metallic fibers and/or endless fibers with an aspect ratio of at least 100:1 in the form of fiber structures providing a framework,
   b) at least one bone cement preparation, comprising resorbable mineral bone cement powder.

16. Use of a set according to claim 15 for producing a bone implant.

17. Implant according to claim 1, characterized in that the fiber structures are aligned in specific three-dimensional directions so as to provide greater reinforcement at points on the contour of the implant with greater stress from the defective area to be repaired.

18. Implant according to claim 1, characterized in that the reinforcing, long metallic fibers and/or endless metallic fibers have a minimum length of 30 mm.

* * * * *